United States Patent
Kwak et al.

(10) Patent No.: US 11,685,900 B2
(45) Date of Patent: Jun. 27, 2023

(54) NANOFIBER-BASED LONG-TERM PRIMARY HEPATOCYTE THREE-DIMENSIONAL CULTURE SYSTEM AND CULTURING METHOD

(71) Applicant: NANOFAENTECH CO., LTD., Gimhae-si (KR)

(72) Inventors: Jong-Young Kwak, Suwon-si (KR); Min Gyu Song, Tongyeong-si (KR); So Hee Kim, Seoul (KR); Min Ho Choi, Seoul (KR)

(73) Assignee: NANOFAENTECH CO., LTD., Gimhae-si (KR)

( * ) Notice: Subject to any disclaimer, the term of this patent is extended or adjusted under 35 U.S.C. 154(b) by 405 days.

(21) Appl. No.: 16/649,986

(22) PCT Filed: Sep. 21, 2018

(86) PCT No.: PCT/KR2018/011215
§ 371 (c)(1),
(2) Date: Mar. 24, 2020

(87) PCT Pub. No.: WO2019/059702
PCT Pub. Date: Mar. 28, 2019

(65) Prior Publication Data
US 2020/0239851 A1    Jul. 30, 2020

(30) Foreign Application Priority Data

Sep. 25, 2017  (KR) .................. 10-2017-0123545
Sep. 17, 2018  (KR) .................. 10-2018-0110880

(51) Int. Cl.
*C12N 5/071* (2010.01)
*C12N 5/00* (2006.01)
*G01N 33/50* (2006.01)

(52) U.S. Cl.
CPC .......... *C12N 5/0671* (2013.01); *C12N 5/0062* (2013.01); *C12N 5/0068* (2013.01);
(Continued)

(58) Field of Classification Search
CPC .. C12N 5/0671; C12N 5/0062; C12N 5/0068; C12N 2533/30
See application file for complete search history.

(56) References Cited

U.S. PATENT DOCUMENTS 9,163,331 B2 * 10/2015 Atala .................. C12N 5/0691
2006/0019326 A1    1/2006 Vacanti et al.

FOREIGN PATENT DOCUMENTS

KR    10-1458425 B1    11/2014
KR    10-1665918 B1    10/2016
(Continued)

OTHER PUBLICATIONS

Otsuka et al. Micropatterned co-culture of hepatocyte spheroids layered on non-parenchymal cells to understand heterotypic cellular interactions. Sci. Technol. Adv. Mater. 14. p. 1-10 (Year: 2013).*
(Continued)

*Primary Examiner* — Taeyoon Kim
(74) *Attorney, Agent, or Firm* — Revolution IP, PLLC

(57) ABSTRACT

Disclosed is a nanofiber-based long-term primary hepatocyte culture system and a culture method, wherein the primary hepatocyte culture system has an advantage that it can culture cells in three-dimensions in vitro to maintain the original physiological activity of low proliferative primary hepatocytes for a long time by co-culturing indirectly by separating primary hepatocytes and hepatic non-parenchymal cells with a support consisting of nanofibers therebetween without direct co-culture.

11 Claims, 12 Drawing Sheets

(52) U.S. Cl.
CPC ..... *G01N 33/5008* (2013.01); *G01N 33/5091* (2013.01); *C12N 2533/30* (2013.01); *C12N 2533/40* (2013.01); *C12N 2533/70* (2013.01)

(56) References Cited

FOREIGN PATENT DOCUMENTS

| KR | 10-1684698 | B1 | | 12/2016 | |
|---|---|---|---|---|---|
| WO | 03-082145 | A2 | | 10/2003 | |
| WO | WO-2004031244 | A1 | * | 4/2004 | ............... C07H 1/00 |
| WO | WO-2006059953 | A1 | * | 6/2006 | ............ C12N 5/067 |
| WO | 2014-151921 | A1 | | 9/2014 | |
| WO | 2015-182159 | A1 | | 12/2015 | |
| WO | 2017-126758 | A1 | | 7/2017 | |

OTHER PUBLICATIONS

Bale et al. Isolation and co-culture of rat parenchymal and non-parenchymal liver cells to evaluate cellular interactions and response. Scientific Reports 6:25329, p. 1-10 (Year: 2016).*

Cho et al. Fucoidan protects hepatocytes from apoptosis and inhibits invasion of hepatocellularcarcinoma by up-regulatingp42/44MAPK-dependent NDRG-1/CAP43. Acta Pharmaceutica Sinica B 2015;5(6):544-553 (Year: 2015).*

Diaz-Gomez et al. Biodegradable electrospun nanofibers coated with platelet-rich plasma for cell adhesion and proliferation. Materials Science and Engineering C 40 (2014) 180-188 (Year:2014).*

Huang et al. Comparison of cell behavior on pva/pva-gelatin electrospun nanofibers with random and aligned configuration. Scientific Reports 6:37960, p. 1-8 (Year: 2016).*

International Search Report for PCT/KR2018/011215 dated May 28, 2019 from Korean Intellectual Property Office.

Lee, Ji Seok et al., "Fabrication of electrospun biocomposites comprising polycaprolactone/fucoidan for tissue regeneration", Carbohydrate Polymers, 2012, vol. 90, No. 1, pp. 181-188.

Goonoo, N et al., "In vitro and in vivo cytocompatibility of electrospun nanofiber scaffolds for tissue engineering applications", RSC Adv. 2014, vol. 4, No. 60, pp. 31618-31642.

Zhang, Weijie et al., "Electrospinning of Fucoidan/Chitosan/Poly(vinyl alcohol) Scaffolds for Vascular Tissue Engineering", Fibers and Polymers. May 2017, vol. 18, No. 5, pp. 922-932.

Han, Sinung, "Studies on the 3D culture of mouse primary hepatocyte using nanofiber scaffold", Graduate School of Global Pharmaceutical Industry and Clinical Pharmacy Department of Medicine. Master's Thesis.

Oct. 23, 2017, pp. 1-5, non-official translation (Biospectator (online newspaper article). Prediction of Toxicity of New Drug Using Hepatocelluar 3D Culture Technology). Retrieved from the Internet: <http://www.biospectator. com/view/news_print.php?varAtcId=4240>.

* cited by examiner

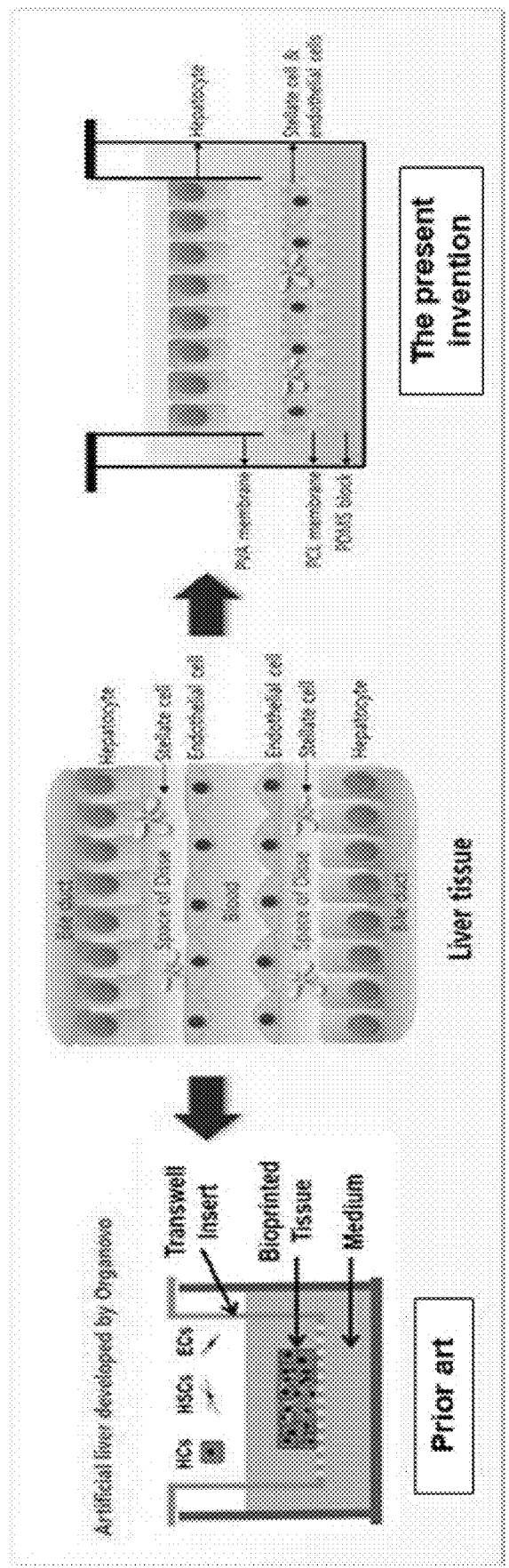
[FIG. 1]

[FIG. 2]
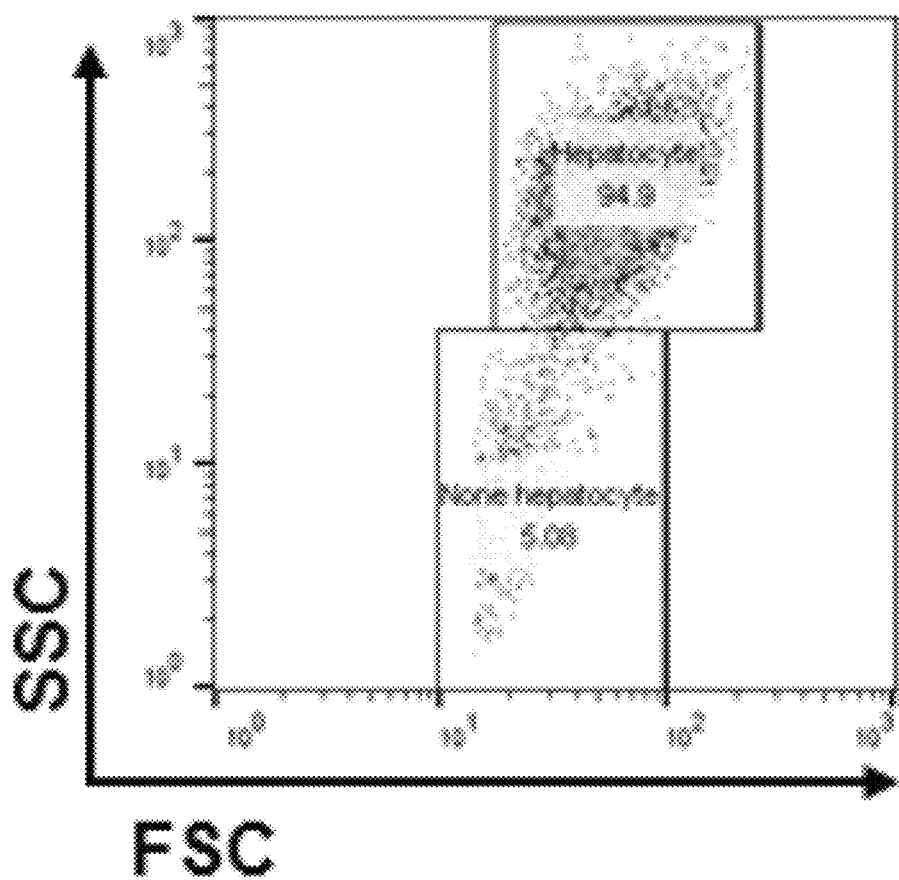
[FIG. 3]
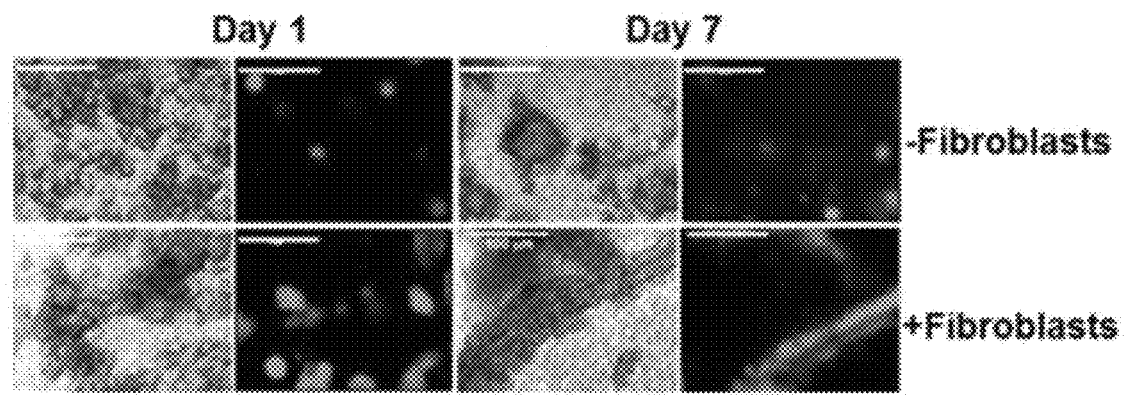

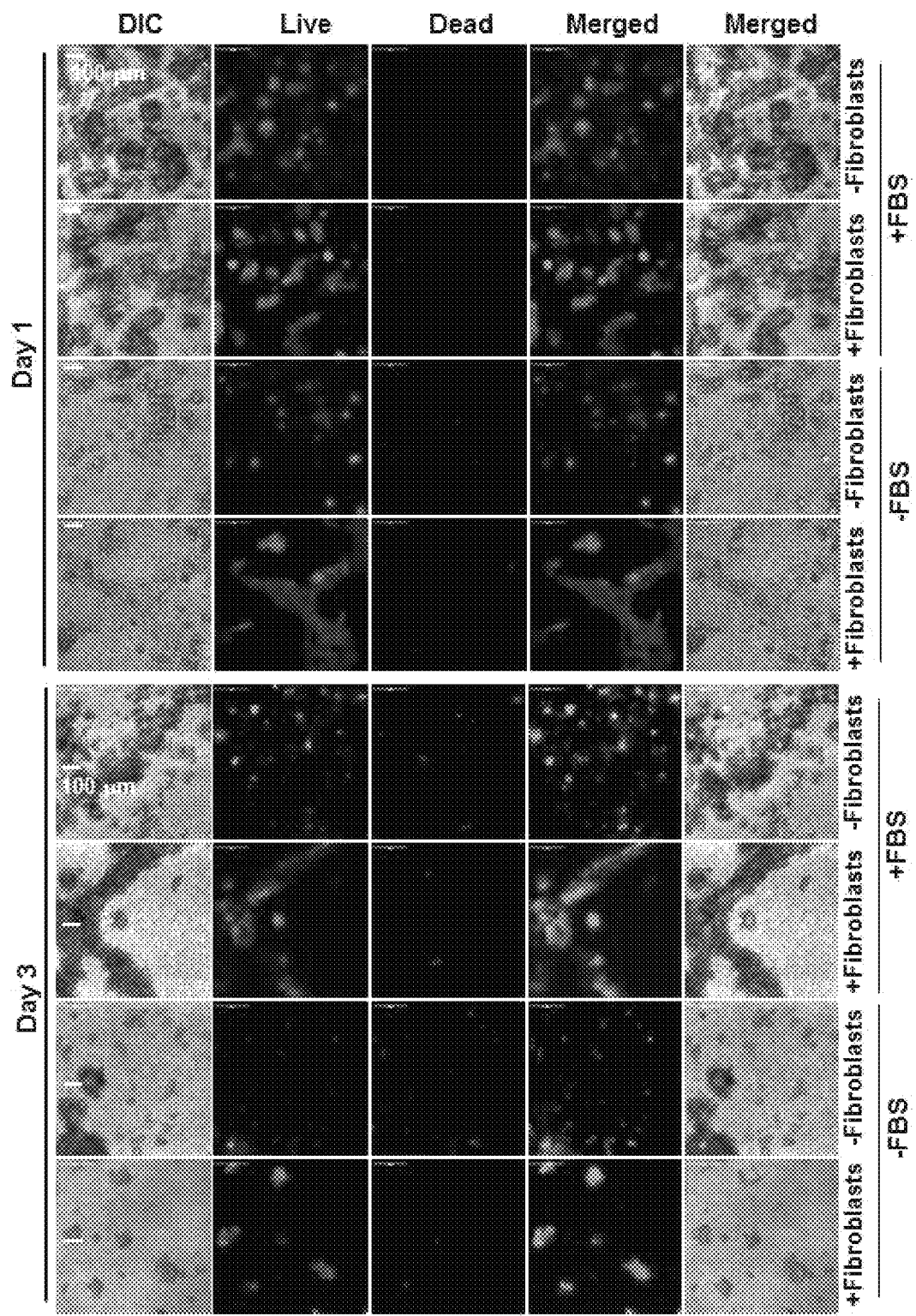
[FIG. 4]

[FIG. 5]
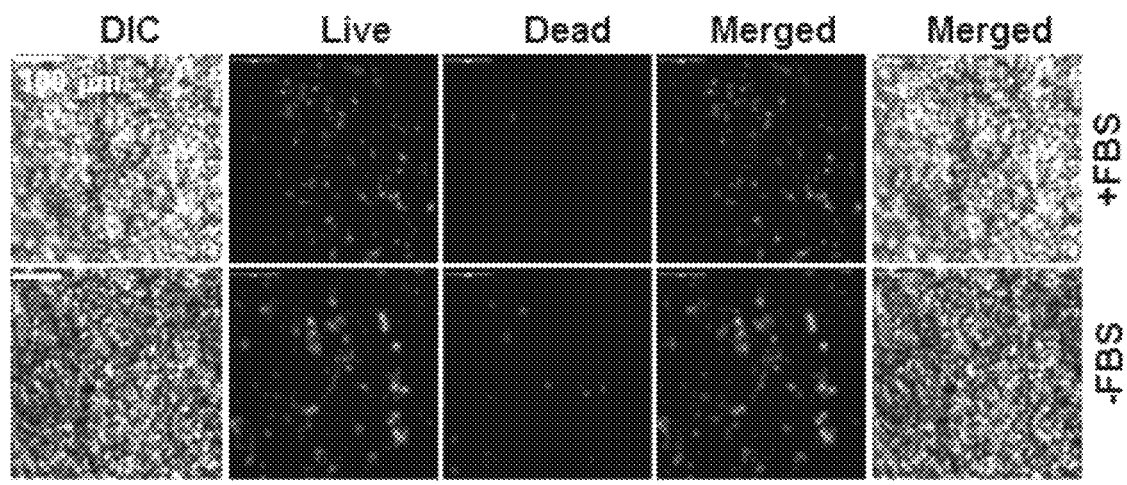
[FIG. 6]
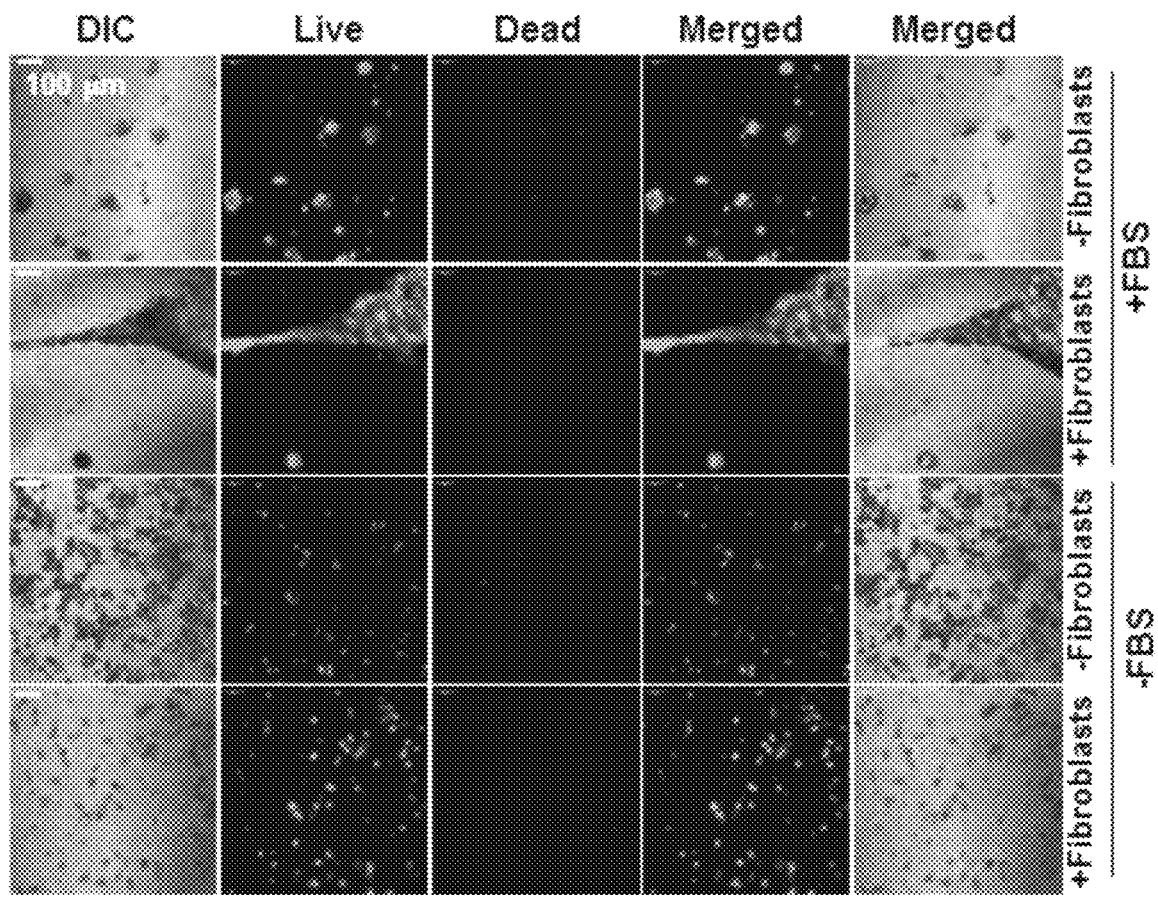

[FIG. 7]
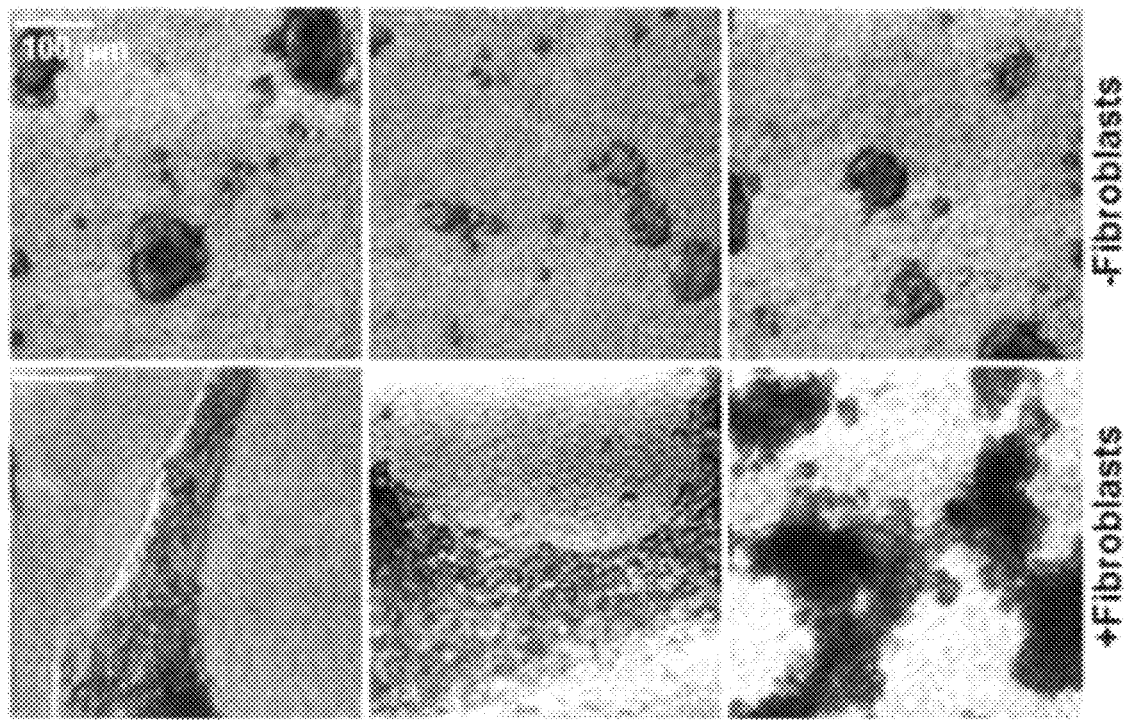
[FIG. 8]
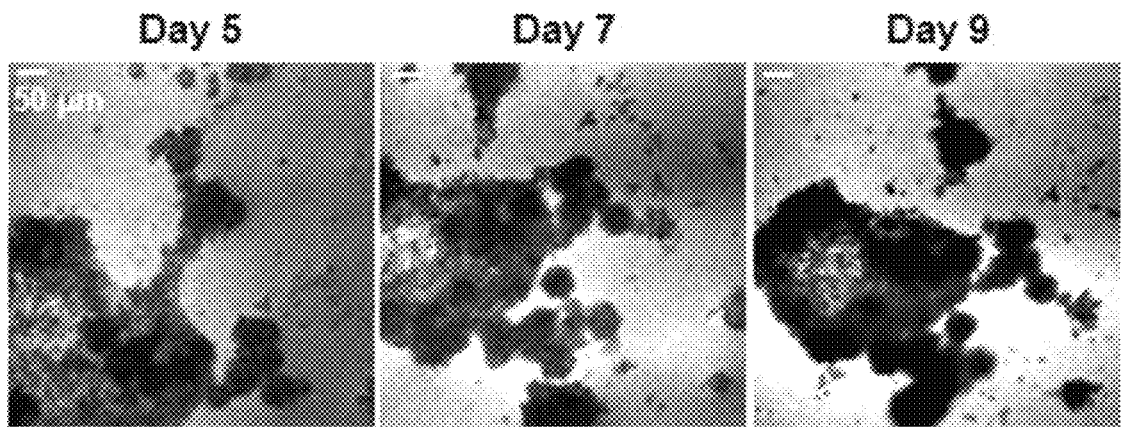

[FIG. 9]
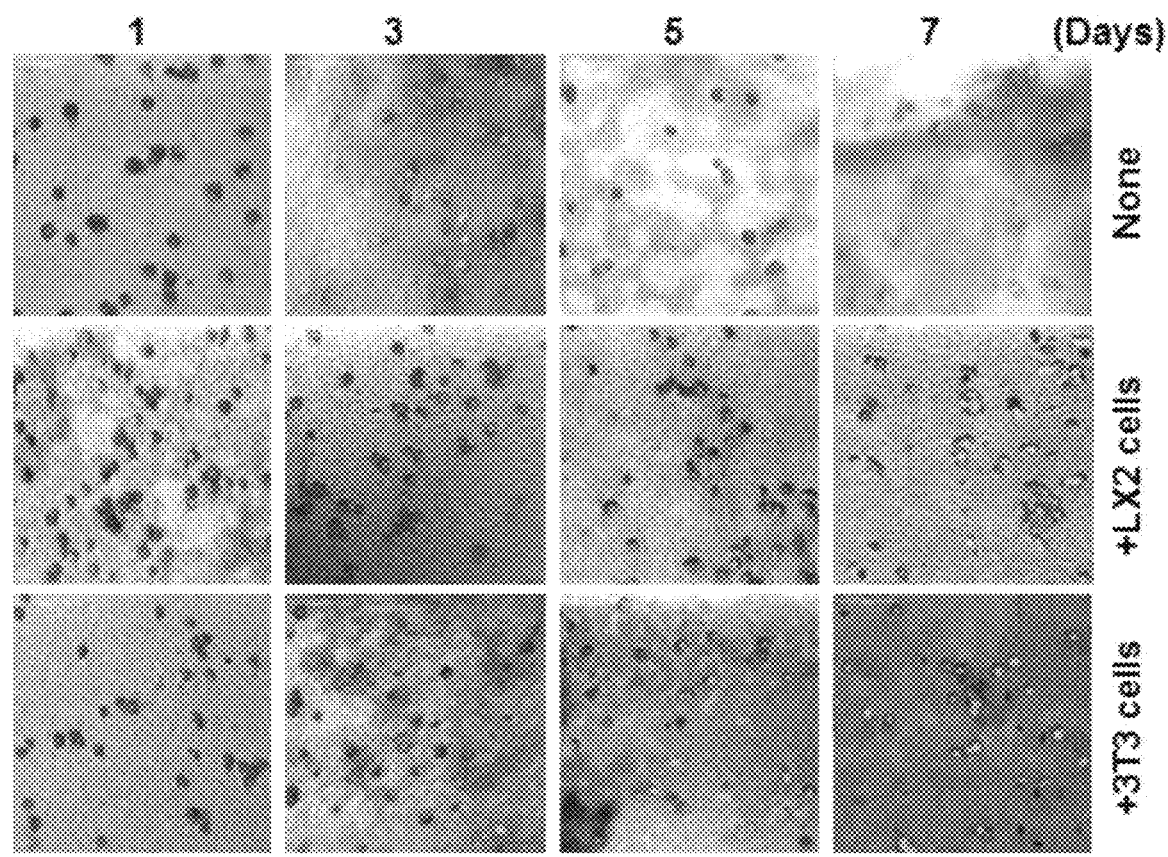

[FIG. 10]
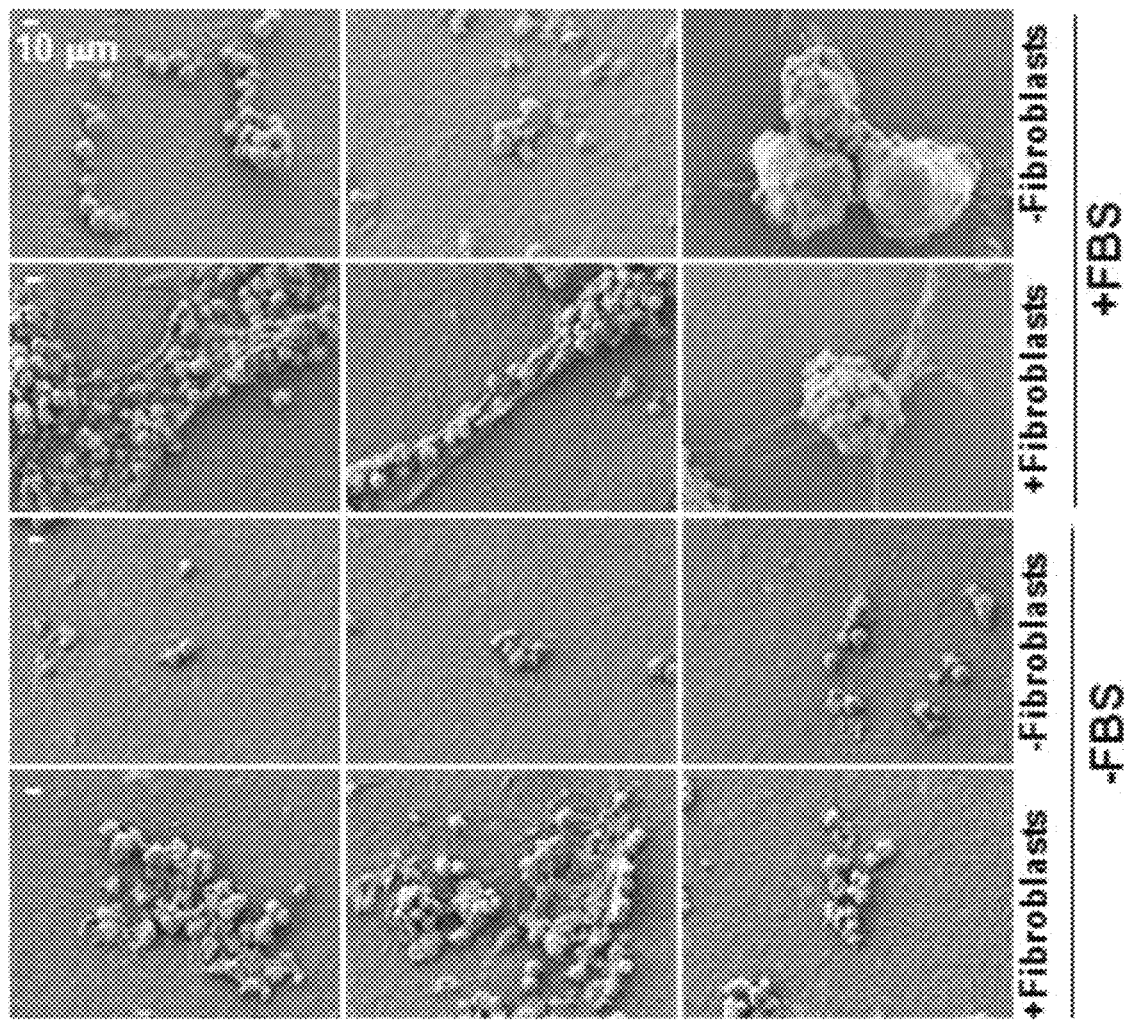

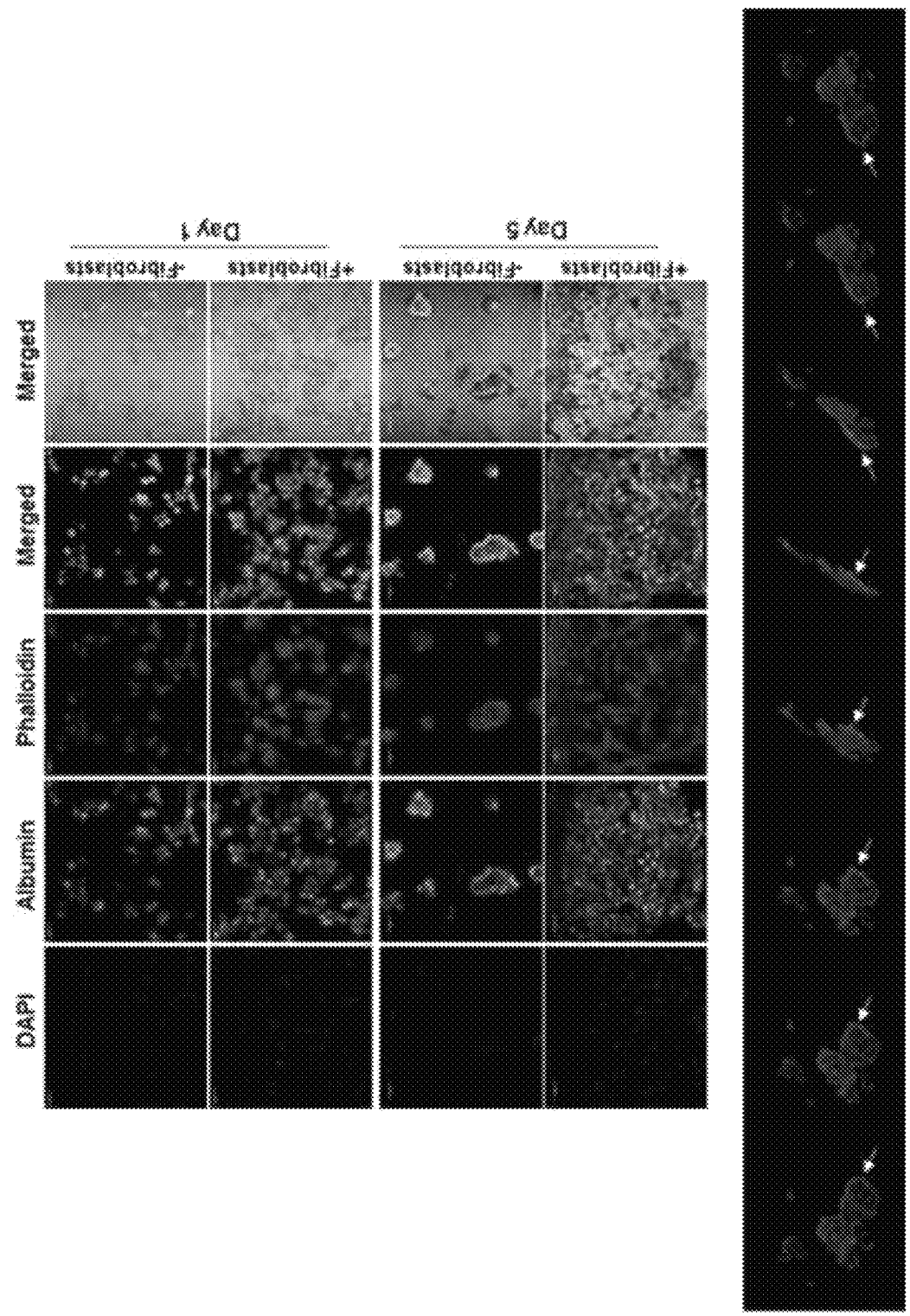
[FIG. 11]

[FIG. 12]
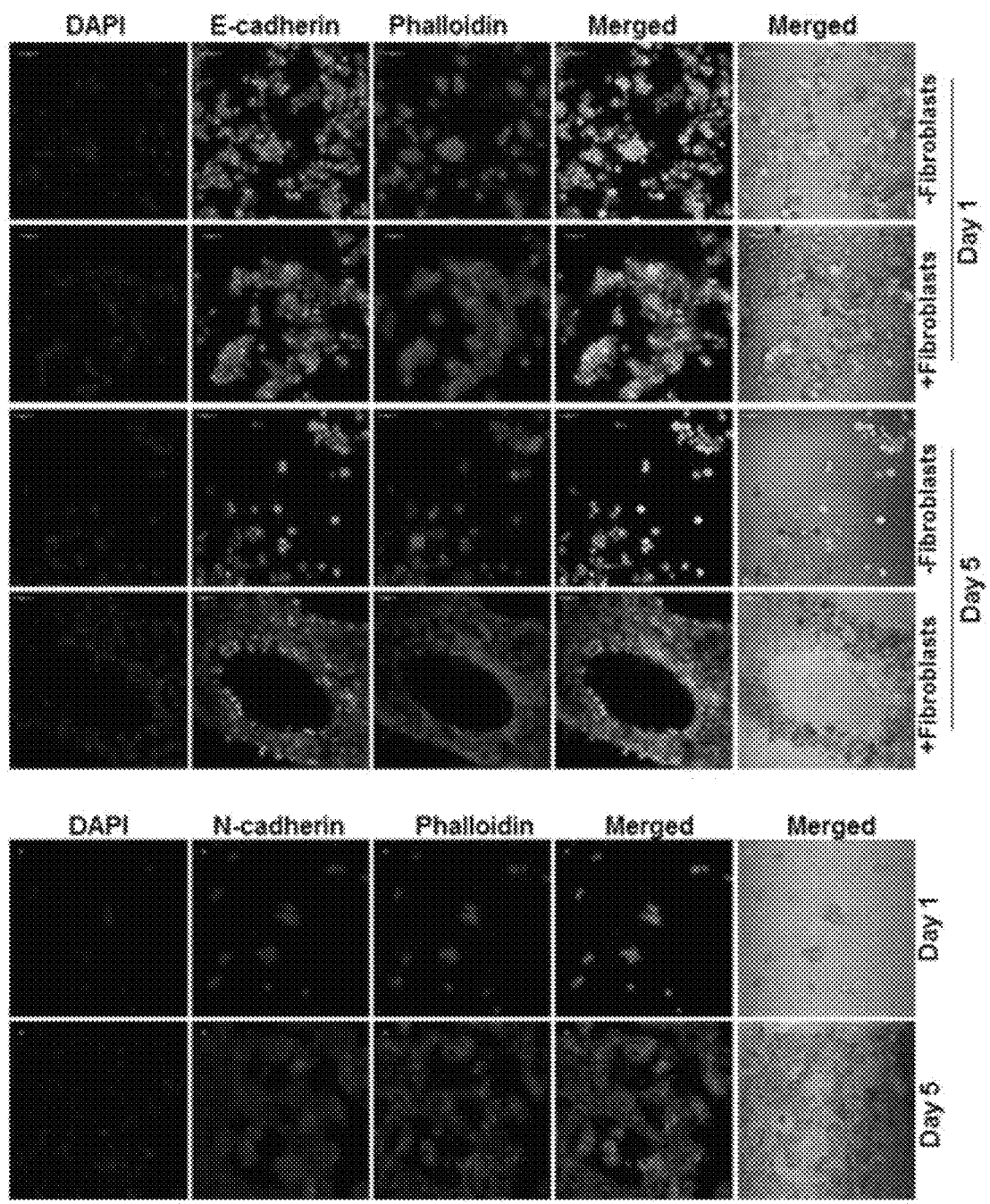

[FIG. 13]
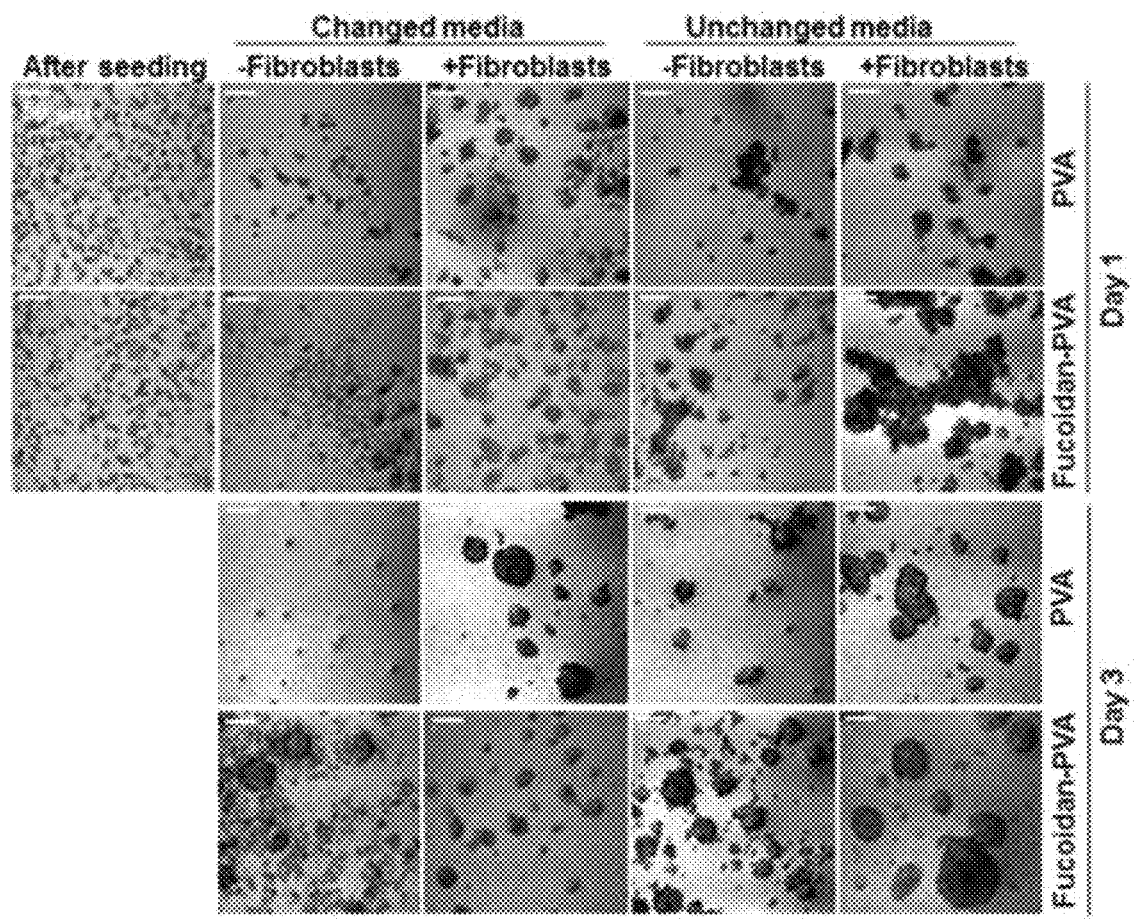
[FIG. 14]
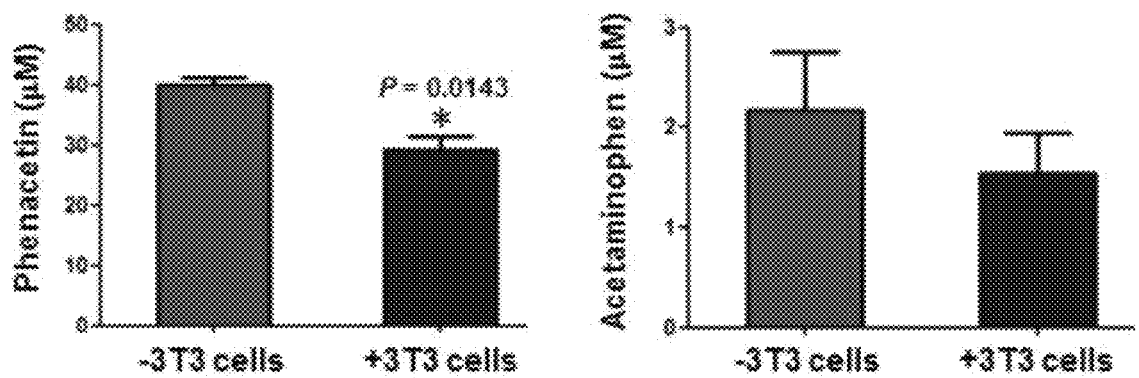

[FIG. 15]
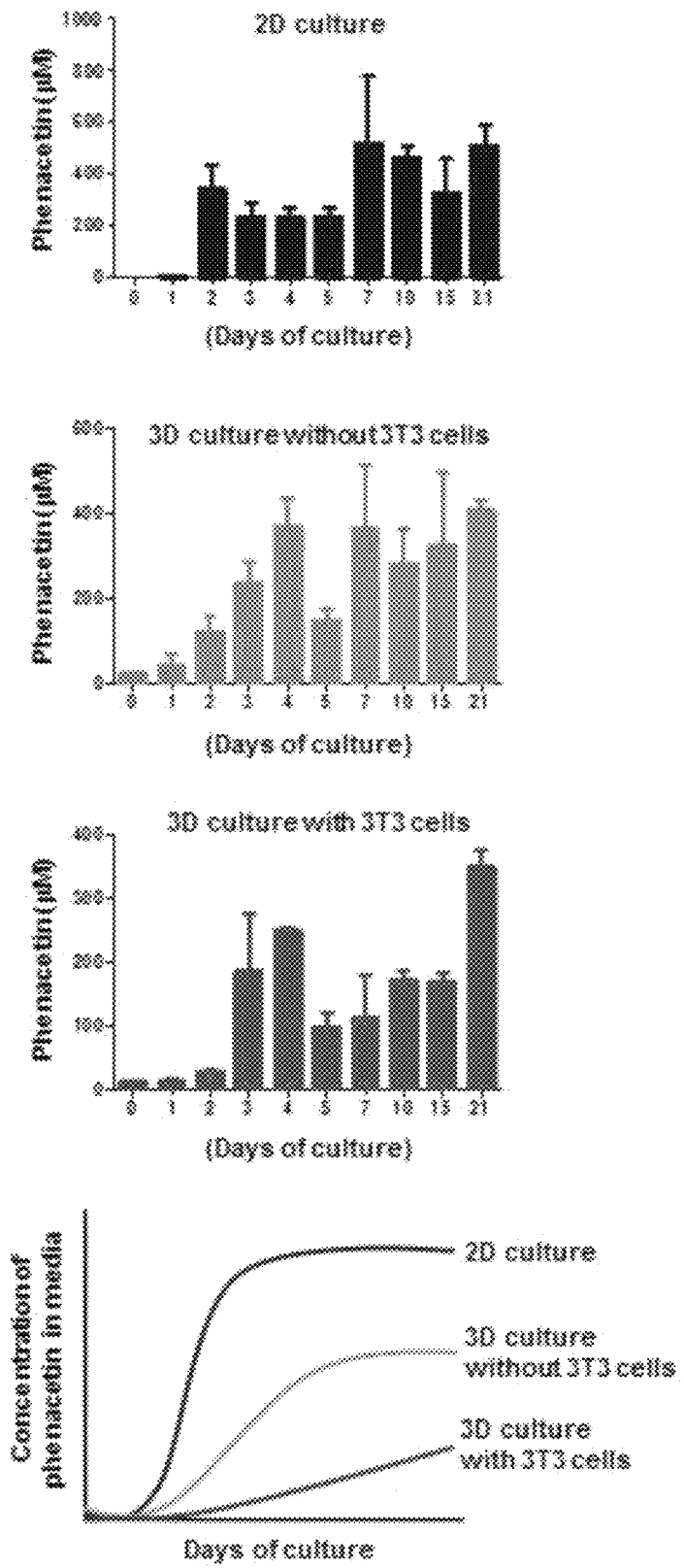

[FIG. 16]
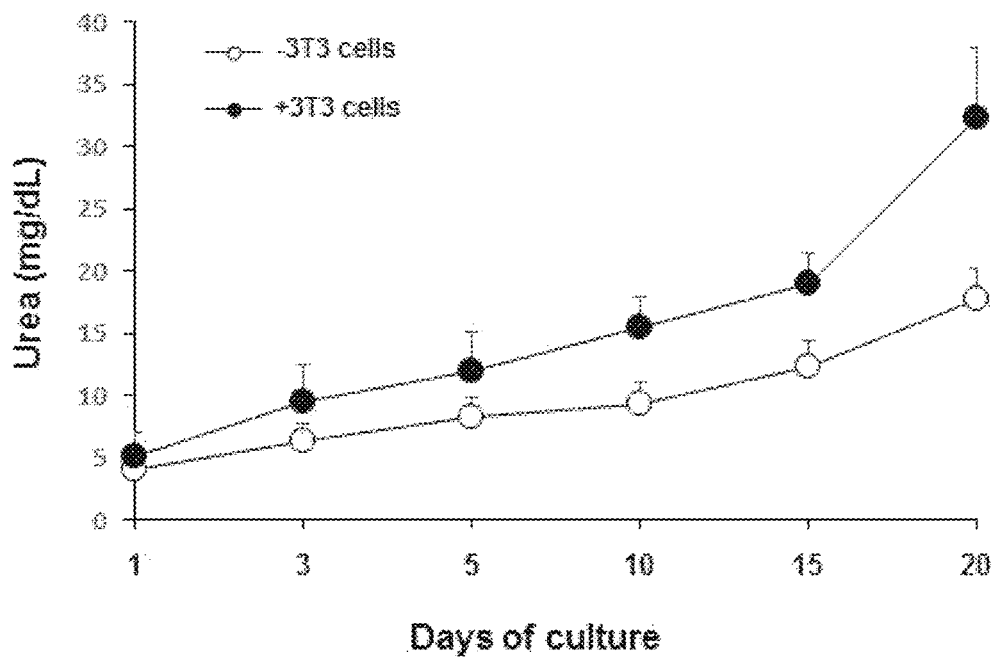
[FIG. 17]
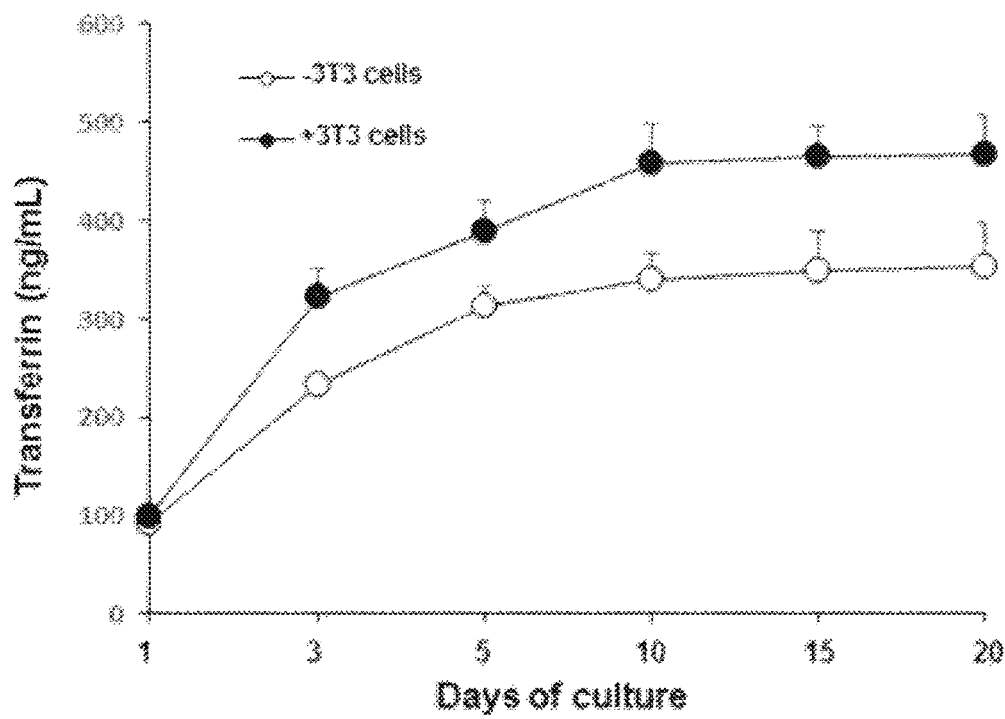

NANOFIBER-BASED LONG-TERM PRIMARY HEPATOCYTE THREE-DIMENSIONAL CULTURE SYSTEM AND CULTURING METHOD

TECHNICAL FIELD

The present invention relates to a nanofiber-based long-term primary hepatocyte culture system and a culturing method, characterized in indirect three-dimensional co-culture without direct co-culture by separating human primary hepatocytes and hepatic non-parenchymal cells with a support consisting of nanofibers therebetween.

The present invention was carried out with the support of a research project of "Functioning and practical use of self-damage defense immune-network developed in nano-chip" of future promising convergence technology pioneer supported by Ministry of Science and ICT (Project number: 2015-001923, Host: Ajou University Industry-Academic Cooperation Foundation, Research period: Mar. 1, 2015—Feb. 28, 2018) and a research project of "3D Immunochip-based pre-clinical development platform" of R&D project supported by the Ministry of Health and Welfare (Project number: HI16C0992, Host: Ajou University Industry-Academic Cooperation Foundation, Research period: Apr. 1, 2016-Dec. 31, 2024).

BACKGROUND ART

The liver, which has functions of drug metabolism, glyconeogenesis, and lipid metabolism, plays a variety of important roles in vivo. Hepatocytes culture is very important for the study of various liver functions or the establishment of assays for metabolic detoxification of various drugs including carcinogens.

So far, in the culture of hepatocytes, general hepatocytes or primary cultured hepatocytes have been used as culture cells, however, since many of the general hepatocytes are hepatocarcinoma cells and have different properties from the parenchymal cells of the liver, experimental results obtained using hepatic cancer cells were difficult to accept as they reflect life phenomena such as metabolism in living organisms, and primary cultured hepatocytes are close to hepatocytes to have been recognized preferable as cultured cells. In addition, primary cultured hepatocytes are useful for measuring the effects (medicament, toxicity, etc.) of various drugs or chemicals such as toxins in the living body, or investigating what properties of reaction metabolites, e.g. a harmful substance such as a carcinogenic substance are obtained by the action of cytochrome P-450 in the living body, and thus a method of culturing primary cultured hepatocytes having a long-term function is very important.

However, hepatocytes die within 1 to 2 days of primary culture and they should be cultured in a medium composition containing special media such as William's E medium, dexamethasone, insulin, etc. and even if hepatocytes survive, there is a problem that the intrinsic physiological activity and cell adhesion of the living body are significantly reduced. There is a spheroid culture technique of hepatocytes (WO2015182159), but this technique also requires the special culture solution described above. Therefore, there is a need for the development of primary hepatocyte culture technology having a long-term intrinsic physiological activity.

Because clinical trials have risks and ethical issues about trials, cell or animal experiments are being conducted as alternatives. In vitro and preclinical animal testing alternative liver tissue-specific toxicity marker measurement techniques need to be developed. Since the culture of hepatocytes is still largely at two-dimensional level, the cell survival time is short, and the cell function is rapidly decreased after the culture, thereby limiting the measurement of various responses of the living body.

However, since there is still no three-dimensional hepatocyte culture technology that can reflect the characteristics of biological, physiological and chemical reactions of human liver tissues, there is difficulty in various toxicology testing and drug metabolism experiments.

It is also necessary to develop a hepatocyte culture system capable of measuring metabolized drug metabolites in the liver. For this purpose, it should be a culture condition in which the survival of hepatocytes can be maintained to the maximum. The use of hepatocytes cultured in three dimensions can produce results that are closer to that of drug metabolism or toxicity testing in actual human body.

Conventional two-dimensional culture is a sandwich method in which cells are seeded in a collagen-coated culture dish and matrigel is placed on the cells again, however, in this culture, long-term culture of hepatocytes is difficult and various growth factors or drugs are added to William's E medium, thereby being an expensive culture method and it has a limitation of two-dimensional culture. In addition, recently, hepatocytes, vascular endothelial cells and fibroblasts have been co-cultured directly as a bioprinting technique to perform liver tissue-like three-dimensional culture (WO2014151921), but there is no technique for simulating the living liver tissue microenvironment by three-dimensional indirect co-culture in a chamber under a well-controlled environment while attached to another layer of nanofiber support.

DISCLOSURE

Technical Problem

Accordingly, an object of the present invention is to provide a primary hepatocyte co-culture system and a three-dimensional culture method that can be cultured for a long period of time by improving low viability and have an original physiological activity.

Technical Solution

In order to solve the above problems, the present invention provides a three-dimensional culture system of primary hepatocyte comprising: a first layer in which primary hepatocytes are cultured on a support consisting of polyvinyl alcohol (PVA) nanofibers; and a second layer in which liver non-parenchymal cells are cultured on a support consisting of polycaprolactone (PCL) nanofibers, wherein the first layer and the second layer are stacked adjacently.

In addition, the present invention provides a three-dimensional culture method of primary hepatocyte comprising co-culturing indirectly by separating primary hepatocytes and hepatic non-parenchymal cells with a support consisting of nanofibers therebetween without direct co-culture.

Advantageous Effects

The primary hepatocyte culture system according to the present invention has an advantage that can be cultured in three dimensions in vitro to maintain intact physiological activity of primary hepatocytes having low survival by co-culturing indirectly by separating primary hepatocytes and hepatic non-parenchymal cells with a support consisting of nanofibers therebetween without direct co-culture. The primary hepatocyte culture system is a hepatic tissue-like environment, and it is possible to culture primary hepatocytes easily at low cost without using expensive serum, and it can be used in various fields such as drug-drug interaction analysis through induction and inhibition of hepatic drug metabolism enzyme (cytochrome P450 enzyme), functional uptake analysis of liver transporter, drug-induced liver injury analysis, and in vitro hepatocyte model for fatty liver disease, and screening for medicine of fatty liver disease using the same.

DESCRIPTION OF DRAWINGS

FIG. 1 shows an indirect two-layer three-dimensional hepatocyte co-culture system according to the present invention (left, conventional co-culture system; middle. liver tissue; right, co-culture system according to the present invention).

FIG. 2 shows results of measuring the purity of hepatocytes by flow cytometry after isolation of primary hepatocytes of mouse used in the present invention.

FIG. 3 shows the survival rate of primary hepatocytes for 7 days using an indirect three-dimensional hepatocyte co-culture system according to the present invention.

FIG. 4 shows the culture state and survival rate of primary hepatocytes for 1 and 3 days in culture medium with or without bovine serum using an indirect three-dimensional hepatocyte co-culture system according to the present invention.

FIG. 5 shows the culture state and survival rate of NIH3T3 fibroblasts for 3 days in culture medium with or without bovine serum using an indirect three-dimensional hepatocyte co-culture system according to the present invention.

FIG. 6 shows the culture state and survival rate of primary hepatocytes for 5 days in culture medium with or without bovine serum using an indirect three-dimensional hepatocyte co-culture system according to the present invention.

FIG. 7 shows results observing by the differential interference contrast (DIC) microscopic through transparent nanofibers of the difference between the degree of formation of hepatocyte aggregates in the co-cultured primary hepatocytes with fibroblasts and the cultured primary hepatocytes alone for 5 days using an indirect three-dimensional hepatocyte co-culture system according to the present invention.

FIG. 8 shows the change of cell aggregates in the same region in real time in the co-cultured primary hepatocytes with fibroblasts for 5 to 9 days using an indirect three-dimensional hepatocyte co-culture system according to the present invention.

FIG. 9 shows the survival rate of primary hepatocytes cultured for 7 days at a density such that no aggregation occurs in co-culture of human hepatic stellate LX-2 cells as a non-parenchymal cell and 3T3 mouse fibroblasts using an indirect three-dimensional hepatocyte co-culture system according to the present invention.

FIG. 10 shows a scanning electron microscope image confirming the cell state in the nanofibers after 5 days of incubation of primary hepatocytes in a medium with or without bovine serum using an indirect three-dimensional hepatocyte co-culture system according to the present invention.

FIG. 11 shows a confocal microscope result of the expression level of intracellular albumin in the co-cultured primary hepatocytes with fibroblasts and the cultured primary hepatocytes alone for 5 days using an indirect three-dimensional hepatocyte co-culture system according to the present invention.

FIG. 12 shows a confocal microscope result of the degree of intracellular E-cadherin expression in the co-cultured primary hepatocytes with fibroblasts and the cultured primary hepatocytes alone for 5 days using an indirect three-dimensional hepatocyte co-culture system according to the present invention.

FIG. 13 shows the degree of cell adhesion in the co-cultured primary hepatocytes with fibroblasts and the cultured primary hepatocytes alone for 1 and 3 days using fucoidan-containing PVA nanofibers to enhance cell adhesion of the PVA nanofibers for hepatocyte culture constituting an indirect three-dimensional hepatocyte co-culture system according to the present invention.

FIG. 14 shows results measuring the concentration of acetaminophen, which is a metabolite of phenacetin and phenacetin remaining in the culture medium in 24 hours after the administration of phenacetin to primary hepatocytes cultured for 5 days to measure drug metabolism of hepatocytes using an indirect three-dimensional primary hepatocyte co-culture system according to the present invention. The table 1 shows results of comparing the degree of phenacetin metabolism activity calculated based on the number of surviving primary hepatocytes and the concentration of metabolized drug after incubation.

FIG. 15 shows results of measuring the concentration of phenacetin remaining in the culture medium in 24 hours after treatment of phenacetin on primary hepatocytes cultured for a certain period of time to measure the drug metabolism by long-term surviving primary hepatocytes using an indirect three-dimensional primary hepatocyte co-culture system according to the present invention.

FIG. 16 shows results of measuring the concentration of urea secreted in the culture medium of hepatocytes cultured for a certain period of time to measure the function of long-term surviving primary hepatocytes using an indirect three-dimensional primary hepatocyte co-culture system according to the present invention.

FIG. 17 shows results of measuring the concentration of transferrin secreted in the culture medium of hepatocytes cultured for a certain period of time to measure the protein secretion function of long-term surviving primary hepatocytes using an indirect three-dimensional primary hepatocyte co-culture system according to the present invention.

BEST MODE

Hereinafter, the present invention will be described in more detail.

The present inventors have made efforts to solve the problem of low viability of primary hepatocytes and the remarkable deterioration of biological intrinsic physiological activity and cell adhesion in in vitro culture by three-dimensional co-culture in a well-controlled chamber with hepatocytes and non-parenchymal cells (vascular endothelial cells and fibroblasts) attached to different layers of nanofibrous support, respectively and by co-culturing indirectly by separating primary hepatocytes and hepatic non-parenchymal cells with a support consisting of nanofibers therebetween without direct co-culture, as a technique of simulating living liver tissue microenvironment and it has been found that three-dimensional cell culture can be performed in vitro to maintain original physiological activity for long term of low proliferative primary hepatocytes and completed the present invention.

The present invention provides a three-dimensional culture system of primary hepatocyte comprising: a first layer in which primary hepatocytes are cultured on a support consisting of PVA nanofibers; and a second layer in which liver non-parenchymal cells are cultured on a support consisting of PCL nanofibers, wherein the first layer and the second layer are stacked adjacently.

Because the culture system according to the present invention comprises nanofiber support and thus it can prevent direct co-culture between primary hepatocytes and hepatic non-parenchymal cells and induce direct co-culture, there is a problem caused by direct co-culture between primary hepatocytes and hepatic non-parenchymal cells, that for example, fibroblasts grow faster than hepatocytes due to differences in growth rate between primary hepatocytes and hepatic non-parenchymal cells and fibroblasts must be co-cultured by slowing the survival of the fibroblasts, and the original function of the hepatocytes can be lost by the direct co-culture.

Also, the present invention provides the three-dimensional culture method of primary hepatocyte comprising: culturing primary hepatocytes on a support consisting of PVA nanofibers; culturing liver non-parenchymal cells on a support consisting of PCL nanofibers; and stacking the support consisting of PVA nanofibers on which the primary hepatocytes are cultured and the support consisting of PCL nanofibers on which the liver non-parenchymal cells are cultured.

The culture system/culture method according to the present invention can prevent direct co-culture between the primary hepatocytes and the hepatic non-parenchymal cells and induce indirect co-culture.

The primary hepatocytes may be primary cultured hepatocytes derived from humans, rats or mice, but they are not limited thereto.

The hepatic non-parenchymal cells may be at least one selected from the group consisting of hepatic fibroblasts, hepatic blood vessel endothelial cells, hepatic stellate cells and Kupffer cells, but they are not limited thereto.

The culture system/culture method according to the present invention can observe primary hepatocytes in real time due to transparent properties of PVA nanofibers.

The nanofibers may be selected from PVA nanofibers or PCL nanofibers, but they are not limited thereto.

In order to improve the adhesion of primary hepatocytes to the PVA nanofibers, a cell adhesion factor, particularly fucoidan, may be included, but it is not limited thereto.

In order to improve the adhesion of hepatic non-parenchymal cells to the PCL nanofibers, a cell adhesion factor, particularly fucoidan, may be included, but it is not limited thereto.

In the co-culture, the cell ratio of the hepatocytes and the hepatic non-parenchymal cells may be 1:1 to 1:3.

The primary hepatocyte three-dimensional culture method of claim 1, wherein seeding density of the primary hepatocytes is $1 \times 10^4$ to $3 \times 10^4$ cells/cm$^2$, and a disk-shaped spheroid can be formed by culturing while attached on the nanofibers.

In the culture of the primary hepatocytes, hepatocytes may survive in DMEM medium for a long time by replacing various culture mediums in which various drugs are added to William's E culture medium used for the culture of hepatocytes, but it is not limited to DMEM medium.

In addition, the present invention provides a method of analyzing drug-drug interaction through induction and inhibition of hepatic drug metabolism enzyme using the culture system of primary hepatocyte.

The present invention also provides a functional uptake analysis method of drugs by hepatocytes using the primary hepatocyte culture system.

The present invention also provides a method of analyzing liver function using the primary hepatocyte culture system.

Hereinafter, the present invention will be described in detail with reference to the following examples. The examples are only for describing the present invention in more detail and it is obvious to those skilled in the art that that the scope of the present invention is not limited by these examples embodiments in accordance with the gist of the present invention.

<Reference Example 1> Preparation of PVA Nanofibers for Three-Dimensional Hepatocyte Culture PVA nanofibers for three-dimensional hepatocyte culture were prepared according to the method of Korean Patent No. 1665918 and the PVA nanofibers are stable in water, transparent, have excellent cell adhesion, and have an average diameter of 100-200 nm.

<Reference Example 2> Preparation of PCL Nanofibers for Three-Dimensional Hepatocyte Culture Fucoidan-PCL nanofibers for three-dimensional hepatocyte culture were prepared according to the method of Korean Patent No. 1684698 and these fucoidan-PCL nanofibers are useful supports for cell adhesion, cell infiltration and three-dimensional cell growth and have an average diameter of 400-500 nm.

<Example 1> Preparation of NIH3T3 Fibroblast Three-Dimensional Culture Plate 2.5 ml of PDMS solution was added on the bottom of a 24-well plate and half-hardened on a slide warmer preheated to 80° C. However, plates having various sizes without limiting to 24 wells can be used. The adhesive PDMS before it was completely hardened was transferred to room temperature and allowed to cool for 5 minutes. A PCL nanofiber mat cut to a size of 12Ø was attached onto a consistent hardened PDMS. PCL attached plate was sterilized for 18 hours or more in a UV box filled with 1 ml of 70% ethanol. After removing ethanol, 1 ml of cell culture medium was filled, put in a carbon dioxide cell incubator at 37° C. and soaked for 18 hours or more for the use.

<Example 2> Preparation of Hepatocyte Culture Plate

PDMS was spread thinly on a round bottom in which the prepared transwell membrane was removed and half-hardened for 10 to 15 minutes on a slide warmer preheated to 80° C. The adhesive PDMS was transferred to room temperature and allowed to cool for 5 minutes before it was completely hardened. A PVA nanofiber membrane cut to 12Ø was attached to the bottom of the transwell over a consistent half-hardened PDMS. The PVA-attached transwells were treated with HCl-sublimated gas for 1 minute. PVA was stabilized by adding 10 µl of dimethylformamide solution to the reacted transwell. The added dimethylformamide solution was volatilized in air using a fan and dried until PVA returned to its original white color. The dried PVA transwells were used after sterilization for at least 18 hours in a UV box.

<Example 3> Preparation of Mouse Primary Hepatocytes

The primary hepatocytes were prepared by in situ collagenase perfusion. In detail, it is as follows. C57 black/6 mice (4-6 weeks old) were anesthetized with ether and the legs were fixed with pins, followed by abdominal dissection. After confirming the position of the hepatic portal vein and the saphenous vein, the belly were opened, and a catheter was inserted into the hepatic portal vein to inject the perfusate (without $Ca^{2+}$ and $Mg^{2+}$, Hanks balanced salt solution (HBSS) containing 25 mM HEPES, 0.5 mM EGTA, pH 7.4, 1% primosin) into a 50 ml syringe from which a bubble is removed at 2-3 ml per minute.

After confirming that the liver was swollen, the inferior vena cava of the lower part of the liver was simultaneously dissected to release blood. Perfusion was stopped after injecting 50 to 60 ml of HBSS solution at 8 ml/min and confirming sufficient blood loss from the liver. The perfusion solution was changed to a solution in which collagenase was dissolved (medium containing DMEM low glucose containing 100 units of collagen type IV) to perform perfusion. During the perfusion, it was confirmed whether the liver was swollen while tightening and releasing the dissected vein to increase the effect of collagen repeatedly. In the present example, perfusion is performed using a medium containing 100 units of collagen, but it is possible to change about 30% depending on the method, but it is not limited thereto.

Perfusion was stopped after the intercellular tissue was digested by collagenase and confirmed whether the cells in the tissue recovered with tweezers. The diaphragm was removed to separate the liver from other organs, and the liver was transferred to cell culture plates using collagenase perfusate warmed at 37° C. The liver was chopped with tweezers and shaken so that isolated cells flow out of the liver, and dispersed to the cells by pipetting. Then micronized tissue was removed by using cell sieve filtration. Cell suspension (medium containing DMEM low glucose medium and DMEM F 12 medium in a 1:1 mixture with 10% FBS) was mixed and non-parenchymal cells were removed by repeating centrifugation at 50×g, 4° C. for 2 minutes 3 to 5 times.

As shown in FIG. 2, the isolated cells were identified to have a purity of 90% or more using a flow cytometer and cell numbers were measured using hemocytometer, and the survival rate of hepatocytes was measured using trypan blue exclusion and primary hepatocytes were cultured.

<Example 4> Three-Dimensional Primary Hepatocyte Co-Culture System

FIG. 1 illustrates an indirect three-dimensional primary hepatocyte co-culture system according to the present invention (left, conventional co-culture system; middle, liver tissue; right, co-culture system according to the present invention), and although hepatocytes and hepatic non-parenchymal cells were directly co-cultured conventionally using transwell, in the present invention, the growth factors of fibroblasts cultured in the hepatic non-parenchymal cell layer through the indirect co-culture instead of the direct co-culture by separating the hepatocellular layer consisting of hepatocytes and hepatic non-parenchymal cell layer consisting of fibroblasts using nanofibers prepared in Reference Example 1 and/or Reference Example 2, were transferred to the hepatocytes cultured in the hepatocyte layer through nanofibers, so that the nutrients necessary for the growth of hepatocytes were sufficiently provided and hepatocytes and fibroblasts were allowed to grow at similar growth rates.

<Example 5> Cell Staining of Live & Dead Cells

Live & Dead cell staining is performed to confirm the survival rate of the cultured primary hepatocytes. As a commercially available kit for checking survival rate, BIOMAX's EZ-View™ Live/Dead cell staining kit was used. In the case of calcein (Calcein-AM) of the Live & Dead cell staining kit as shown in FIG. 3, FIG. 4, FIG. 5 and FIG. 6, the cells were selectively passed only to the living cells, stained with strong green fluorescence, and propidium Iodide (PI) was introduced through the collapsed cell membrane of dead or damaged cells to stain DNA with red fluorescence. The survival rate of the hepatocytes was measured using these two types of reagents. Calcein and propidium iodide were dissolved in the staining kit at room temperature, and then 3 ml of calcein solution and 2 μl of propidium iodide were mixed with 3 ml of cell culture medium. Survival rate staining of hepatocytes was prepared at 24, 72, 120 and 178 hours of culture. Cells cultured in transwells were transferred to a new 24-well plate, then the medium of cultured cells was carefully removed and each 400 μl of the mixed staining reagent was dispensed. Cells containing staining reagents were incubated for 20 minutes in a cell incubator at 37° C. and 5% $CO_2$. In this Example, the cell staining time is not limited to 20 minutes, and the optimal staining time varies depending on the concentration and type of cells. Live and dead cells among the stained cells were confirmed at wavelengths of 490 nm and 545 nm using the K1-Fluo fluorescence microscope of the nanoscope system.

As shown in FIG. 3, when hepatocytes were co-cultured with 3T3 fibroblasts and cultured for 7 days (+Fibroblasts), the number of surviving cells was maintained and appeared as intercellular aggregates and when hepatocytes were cultured alone (-Fibroblasts), a significant decrease was exhibited at 7 of the number of cells attached to the nanofibers, increasing the percentage of dead cells.

<Example 6> Survival and Morphology of Primary Hepatocytes According to Culture Period Since the survival rate of the cultured primary hepatocytes was maintained at 80% and more even after 7 days of culture, the adhesion, survival, and adhesion patterns of hepatocytes to the nanofibers according to the culture conditions after the seeding of the hepatocytes were observed by differential interference microscope and confocal microscope.

As shown in FIG. 4, in the culture condition (+FBS) containing bovine serum 1 day after primary hepatocyte seeding, the cell death did not occur in the culture of hepatocytes alone or co-culture of the same with fibroblasts, and the cells showed similar patterns in both conditions, but in the culture condition without bovine serum (-FBS), a small number of cells were attached. After 3 days of culture, the number of hepatocytes cultured alone decreased significantly and the number of dead cells has been shown to increase, and the attached cells during co-culture appeared to aggregate with each other and most of the cells survived, but in the culture condition without bovine serum, the cells appeared to be attached to nanofiber surface in a separated form rather than aggregation.

As shown in FIG. 5, when 3T3 cells were cultured in a PCL nanofibrous scaffold having a relatively large pore in the lower chamber together with the liver cells of the upper layer are attached to the cells, most of the cells survived and adhered in the case of containing bovine serum, and even in the absence of bovine serum, at least 80% of the cells showed to survive.

<Example 7> Observation of Aggregation of Co-Cultured Primary Hepatocytes

As shown in FIG. 6, hepatocytes co-cultured with bovine serum formed remarkably large cell aggregates after 5 days of culture, but were shown as small cell aggregates when cultured alone. In the absence of bovine serum, the cell aggregation was further reduced but viable cells were attached to the nanofibers. These aggregates could be easily observed by differential interference microscope and fluorescence staining on transparent PVA nanofibers.

As shown in FIG. 7, various types of cell aggregates of co-cultured hepatocytes and hepatocytes cultured alone were shown. In the case of co-culture, the aggregate size was large in several hundred micrometers, which was attached to the nanofibers and showed spheroid-like shape. In comparison, cell aggregation occurred in the case of single culture, but the size was various sizes of 100 micrometers and less.

As shown in FIG. 8, when the change in hepatocyte aggregation was observed under a differential interference microscope, the spheroidal aggregates were increasing in adherence over the incubation period and then some portions were separated from the large aggregates, and most of the aggregates are attached to the nanofibers, but some of the aggregates are detached from the nanofibers and remain suspended in the culture medium.

As shown in FIG. 9, when $1 \times 10^4$ cells/cm$^2$ of hepatocytes were seeded under conditions in which hepatocyte aggregation did not occur and after 2 hours, the culture medium containing the unattached cells was removed and the culture medium was again added and co-culture was performed, the hepatocytes attached were about ⅕ of the initial number of seeded cells. In most cases, hepatocytes cultured under these conditions showed several surviving cells clustered together, rather than large cell aggregation and when co-cultured with LX-2 hepatic stellate cells or 3T3 fibroblasts, the number of the viable cells attached was significantly large. Therefore, it was found that the degree of cell aggregation differs depending on the number of cells seeded in a certain area of the nanofiber support.

<Example 8> Observation by Scanning Electron Microscopy

The morphology of hepatocytes co-cultured in PVA nanofibers was used by scanning electron microscopy (SEM) (JSM-6700F, Japan) after platinum coating of nanofibers.

In the electron microscopy of FIG. 10, the hepatocytes were aggregated through very thin fibers, and the cells constituting the aggregate, with the layer such as another thin layer on the nanofibers as the bottom, appear to form spheroids, consisting of cells from a single layer to several layers. Hepatocytes that are not co-cultured formed the spherical spheroids and cultured hepatocytes without bovine serum appeared smaller.

<Example 9> Albumin, Actin and Cadherin Fluorescence-Staining Analysis

After incubating the mouse primary hepatocytes in a three-dimensional co-culture model for a period of time, albumin, F-actin and E-cadherin staining were performed in the cytoplasm of the cells on PVA nanofiber membrane attached to the upper chamber. To this end, the nanofiber membranes separated from the 24-well plate were placed in 4% paraformaldehyde fixing solution and then fixed at room temperature for 20 minutes. After washing twice with phosphate buffer solution, it was permeabilized with 0.1% Triton X-100 (Sigma-Aldrich) solution at room temperature for 5 minutes and washed twice with phosphate buffer solution. To remove non-specific staining, blocking with 0.2% bovine serum albumin solution (Sigma-Aldrich) at room temperature for 20 minutes was followed by washing twice with phosphate buffer solution. Thereafter, FITC-conjugated anti-albumin antibody, PE-conjugated actin-detecting phalloidin, and FITC-conjugated anti-E-adherin antibody were diluted in a 0.2% bovine albumin solution at a ratio of 1:40 and reacted for 40 minutes and then the cells were washed three times with Tris buffer solution, placed on a slide glass, counterstained with DAPI (Vector Lab) solution for nuclear staining of cells, covered with a cover glass, and sealed and the cells were observed using a confocal laser microscope (K1 nanoscope).

FIG. 11 shows the green fluorescent staining with albumin and red fluorescent staining with phalloidin, and the amount of albumin stained in the living cytoplasm after 5 days of culture does not show a big difference with cells after 1 day of culture, indicating that albumin production remained constantly in these cells. When the expression and distribution of intracellular actin were stained with palloidine, it was mainly detected between cells. The images below of FIG. 11 confirming the shape of the cell mass in three dimensions showed that the cell aggregate forms a spheroid in a disk shape having a thin thickness, and albumin and the like appear uniformly throughout the cell mass.

In FIG. 12, expression patterns of E-cadherin mainly expressed in epithelial cells such as hepatocytes were measured. E-cadherin shown in green fluorescence in the top images of FIG. 12 appeared uniformly in the cytoplasm of hepatocytes cultured for 5 days and did not increase the adhesion surface between cells. As shown in FIG. 9, the palloidine staining was mainly distributed in the intercellular space. This pattern was more clearly seen when the fluorescence staining and the differential interference images were combined. The image below of FIG. 12 illustrates that N-cadherin shown as green fluorescence, showed little increase in the cytoplasm of hepatocytes cultured for 5 days. From these results, cultured hepatocytes continuously expressed E-cadherin and the expression of N-cadherin did not occur, so epithelial-mesenchymal transition did not occur and cell aggregation such as spheroids was similar to the spheroid formed in hydrogel.

<Example 10> Effect of Fucoidan, a Factor Enhancing Cell Adhesion on Hepatocyte Growth As shown in FIG. 13, when after 2 hours of seeding of the hepatocytes, the culture medium was removed (Changed media) and cultured as unchanged (Unchanged media), the degree of forming cell aggregates was different on 1 and 3 days after culturing due to the difference in the number of hepatocytes attached and accordingly, a method of culturing while enhancing cell adhesion was devised.

Fucoidan derived from marine natural products has excellent cell adhesion ability and was subjected to electrospinning by containing fucoidan in a solution containing PVA and a crosslinking agent when preparing PVA nanofibers. In this case, PVA nanofibers containing fucoidan were prepared by electrospinning with PVA/poly acrylic acid/glutaraldehyde solution in which fucoidan (Fucus vesiculosis fucoidan, Sigma) was dissolved at a concentration of 10 mg/ml.

As shown in FIG. 13, hepatocytes cultured in fucoidan-PVA containing fucoidan increased the degree of adhesion and the degree of constituting cell aggregates was also increased.

<Example 11> Drug Metabolism Evaluation

A biomimetic hepatocyte co-culture system was successfully developed by isolating $3\times10^4$ hepatocytes from the mouse and placing them on an insert equipped with PVA using a transwell and co-culturing 3T3 cells under DMEM medium, and after culturing hepatocytes in PVA nanofibers and incubating 3T3 fibroblasts in PCL nanofibers for a period of time, phenacetin at 50 μM or 500 μM was treated and the remaining drug concentration after 24 hours was measured by high performance liquid chromatography (HPLC) and the degree of drug metabolism was compared with the conventional two-dimensional primary hepatocyte culture.

As shown in FIG. 14, phenacetin which is known as a representative substrate of CYP1A2, was supplemented at a concentration of 50 μM in 5 days after treatment with primary hepatocytes alone or co-culture with 3T3 cells in the lower layer and the medium was removed after 24 hours and the concentrations of phenacetin and acetaminophen, metabolites of CYP1A2, were analyzed. Fifty μL of the sample to be quantified and 100 μL of acetonitrile were mixed, centrifuged at 14000 rpm for 10 minutes and the obtained supernatant (130 μL) was dried in nitrogen gas and was dissolved in a solution (10 mM potassium phosphate: acetonitrile, 65%:35% (v/v)) and measured by HPLC (Shimazu Prominence LC-20A) at flow rate of 1 mL/min and at an absorbance of 245 nm for 10 minutes. After 1 day of culture, the concentration of phenacetin remaining in the culture was markedly decreased since the primary hepatocytes can metabolize phenacetin under all culture conditions. The primary hepatocytes cultured for 2 days in two-dimensional culture conditions showed a sharp decrease in the survival rate and the amount of metabolized phenacetin was significantly reduced, indicating that high concentrations of drug remained in the culture medium, but in comparison, primary hepatocytes cultured in three-dimension showed a decrease of 75% to 85% of the drug administered. In addition, when treated with phenacetin in primary hepatocyte culture co-cultured with fibroblasts (3T3), the concentration of phenacetin remaining in the culture medium was significantly decreased compared with that of hepatocytes cultured alone. These results suggest that the metabolism of drugs is sufficiently induced by primary hepatocytes cultured in 3D culture conditions for a long time. In addition, when analyzing the concentration of acetaminophen, a metabolite of CYP1A2, acetaminophen, which is a metabolite, proceeds directly to the next metabolite, glucuronide conjugate or sulfate conjugate, thus the remaining amount of acetaminophen was very small and there was no significant difference between the two groups.

As shown in Table 1, since primary hepatocytes and fibroblasts were indirectly co-cultured, advantageously, the metabolic activity of drugs was directly compared by measuring the concentration of metabolized phenacetin to the number of cells remaining in the upper layer. Compared with such indirect co-culture system, the direct co-culture of various stromal cells including hepatocytes and fibroblasts and the like is very difficult to measure its activity in drug metabolism by primary hepatocytes in which two or more types of cells are mixed and cultured by fibroblast growth. Therefore, in vitro system through non-indirect co-culture system is considered to be the most suitable to implement the measurement of drug metabolic activity in vivo.

As shown in FIG. 15, the long-term cultured primary hepatocytes were treated with phenacetin (500 μM) to compare the degree of metabolism after 24 hours. In two-dimensional culture, the primary hepatocytes were treated with the drug after 1 day of cell culture, and the concentration detected in the culture medium was 350 μM, which had some degree of drug metabolism, but after 3 days of culture, most of the primary hepatocytes died and the drug remained in the culture medium. The amount of added drug appeared to remain. In the three-dimensional culture, the survival rate of primary hepatocytes was maintained at 80% after 15 days of culture, and the concentration of phenacetin detected in the culture was about 350 μM to 400 μM. Especially, when fibroblasts (3T3) were co-cultured, phenacetin of about 200 μM was measured after 15 days of culture, indicating higher drug metabolic efficiency. Therefore, when the drug treated in the cultured primary hepatocytes is metabolized as shown in the images below FIG. 15, in two-dimensional culture, the metabolism of the drug is performed only for 1-2 days after the culture, but in the three-dimensional culture, it can be seen that the drug has a continuous metabolic ability compared to the two-dimensional culture.

TABLE 1

| | Unit | −3T3 cells | +3T3 cells |
|---|---|---|---|
| Concentration of phenacetin | μM | 40.0 ± 2.5 | 29.3 ± 4.8 |
| Media volume | μL | 500 | 500 |
| Cell numbers of hepatocytes | Cells | 18,300 ± 2,500 | |

<Example 12> Measurement of Urea and Transferrin Secretion

As shown in FIG. 16, the amount of urea secreted from cultured hepatocytes ($1\times10^4$) was measured using a QuantiChrom™ Urea Assay Kit (BioAssay Systems, USA) to measure the function of primary hepatocytes. The amount of urea secreted into the culture medium increased steadily in hepatocytes cultured for 20 days and when co-cultured with fibroblasts (3T3) ($1\times10^4$), the secretion of urea increased more than in cultured hepatocytes alone, thereby indicating that hepatocyte function is maintained.

The amount of transferrin secreted from primary hepatocytes ($1\times10^4$) cultured as shown in FIG. 17 was measured using an ELISA kit (Abcam, USA). Up to 10 days after culture, transferrin secretion continued to increase, but no further secretion was observed. This tendency was the same in single culture or co-culture and when co-cultured with fibroblast (3T3) cells, the secretion of transferrin was significantly increased as compared to single culture.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A three-dimensional co-culture system of primary hepatocytes and liver non-parenchymal cells comprising:
    a transwell comprising a membrane of polyvinyl alcohol (PVA) nanofibers, wherein the primary hepatocytes are attached to the membrane of PVA nanofibers; and
    a culture plate comprising a support of polycaprolactone (PCL) nanofibers, wherein the liver non-parenchymal cells are attached to the support of PCL nanofibers,
    wherein the transwell and the culture plate are stacked adjacently, and
    wherein the transwell and the culture plate prevent a direct co-culture between the primary hepatocytes and the liver non-parenchymal cells and induce an indirect co- culture.

2. The three-dimensional co-culture system of claim 1, wherein the support of PVA nanofibers comprises a cell adhesion factor so as to improve adhesion of the primary hepatocytes thereon, wherein the cell adhesion factor is fucoidan.

3. The three-dimensional co-culture system of claim 1, wherein the support of PCL nanofibers comprises a cell adhesion factor so as to improve adhesion of the liver non-parenchymal cells thereon, wherein the cell adhesion factor is fucoidan.

4. The three-dimensional co-culture system of claim 1, wherein seeding density of the primary hepatocytes is $1\times10^4$ to $3\times10^4$ cells/cm$^2$.

5. The three-dimensional co-culture system of claim 1, wherein the liver non-parenchymal cells are at least one selected from the group consisting of hepatic fibroblasts, hepatic blood vessel endothelial cells, hepatic stellate cells and Kupffer cells.

6. The three-dimensional culture system of primary hepatocyte of claim 2, wherein the culture system allows observation of primary hepatocytes in real time due to transparent properties of PVA nanofibers.

7. A three-dimensional co-culture method for primary hepatocytes and liver non-parenchymal cells comprising:
    culturing primary hepatocytes on a membrane of PVA nanofibers in a transwell, wherein the primary hepatocytes are attached to the membrane of the PVA nanofibers;
    culturing liver non-parenchymal cells on a support of PCL nanofibers attached to a culture plate;
    stacking the transwell comprising the primary hepatocytes and the culture plate comprising the liver non-parenchymal cells; and
    co-culturing the primary hepatocytes and the liver non-parenchymal cells,
    wherein the transwell and the culture plate prevent a direct co-culture between the primary hepatocytes and the liver non-parenchymal cells and induce an indirect co- culture.

8. The three-dimensional co-culture method of claim 7, wherein the membrane of PVA nanofibers comprises a cell adhesion factor so as to improve adhesion of primary hepatocytes thereon, wherein the cell adhesion factor is fucoidan.

9. The three-dimensional co-culture method of claim 7, wherein the support of PCL nanofibers comprises a cell adhesion factor so as to improve adhesion of liver non-parenchymal cells thereon, wherein the cell adhesion factor is fucoidan.

10. The three-dimensional co-culture method of claim 9, wherein a ratio of the primary hepatocytes and the liver non-parenchymal cells is 1:1 to 1:3.

11. The three-dimensional co-culture method of claim 9, wherein the primary hepatocytes are seeded at $1\times10^4$ to $3\times10^4$ cells/cm$^2$ on the membrane of PVA nanofibers, and the primary hepatocytes form spheroids attached to the membrane of PVA nanofibers.

* * * * *